US006018100A

United States Patent [19]

Rogers

[11] Patent Number: 6,018,100

[45] Date of Patent: Jan. 25, 2000

[54] PROMOTER FOR TRANSGENIC PLANTS

[75] Inventor: Stephen Gary Rogers, St. Louis, Mo.

[73] Assignee: Monsanto Company, St. Louis, Mo.

[21] Appl. No.: 08/597,325

[22] Filed: Feb. 6, 1996

Related U.S. Application Data

[63] Continuation of application No. 08/366,240, Dec. 27, 1994, abandoned, which is a continuation of application No. 08/172,334, Dec. 22, 1993, Pat. No. 5,378,619, which is a continuation-in-part of application No. 07/429,917, Oct. 31, 1989, abandoned.

[51] Int. Cl.[7] .......................... C12N 15/29; C12N 15/82; A01H 4/00; A01H 5/00

[52] U.S. Cl. ......................... 800/205; 800/250; 536/24.1; 536/24.5; 435/320.1; 435/172.3; 435/240.4

[58] Field of Search ................................ 536/24.1, 24.5; 435/320.1, 240.4, 172.3; 800/205, 250

[56] References Cited

U.S. PATENT DOCUMENTS

| | | | |
|---|---|---|---|
| 4,940,835 | 7/1990 | Shah et al. | 800/205 |
| 5,107,065 | 4/1992 | Shewmaker et al. | 800/205 |
| 5,378,619 | 1/1995 | Rogers et al. | 435/172.3 |

FOREIGN PATENT DOCUMENTS

| | | | |
|---|---|---|---|
| 426641 | 8/1991 | European Pat. Off. | C12N 15/82 |

OTHER PUBLICATIONS

Shah et al 1986 Science 233:478–481.

Sanders et al 1987 Nucleic Acids Research 15: 1543–1558.

Richins et al 1987 Nucleic Acids Research 15: 8451–8466.

Shepherd et al 1987 Phytopathology 77(12): 1668–1673.

Gowda et al 1989 (Mar.) J. Cell Biochem 13D: M318 (Abstract).

Wu et al 1988 (Dec.) Phytopathology 78 (12): 1517 (Abstract #38).

*Primary Examiner*—Douglas W. Robinson
*Assistant Examiner*—Thomas Haas
*Attorney, Agent, or Firm*—Dennis R. Hoerner, Jr.; Monsanto Company

[57] ABSTRACT

A full-length transcript promoter from figwort mosaic virus (FMV) is identified and its DNA sequence given. The promoter functions as a strong and uniform promoter for chimeric genes inserted into plant cells. This strong promoter function is exhibited by a histochemical assay in floral buds and by reproductive scores of transgenic plants including the promoter. The promoter preferably includes a 5' leader sequence that may be from the FMV itself or from a heterologous source with respect to the promoter. The promoter is used in a plant cassette vector, a chimeric gene and in methods for transforming plant cells to obtain transgenic plants, plant cells or seeds incorporating the FMV promoter.

9 Claims, 16 Drawing Sheets

```
             SspI
            ------
      TCATCAAAATATTTAGCAGCATTCCAGATTGGGTTCAATCAACAAGGTACGAGCCATATC
6358  --+---------+---------+---------+---------+---------+-------  6417
      AGTAGTTTTATAAATCGTCGTAAGGTCTAACCCAAGTTAGTTGTTCCATGCTCGGTATAG

      ACTTTATTCAAATTGGTATCGCCAAAACCAAGAAGGAACTCCCATCCTCAAAGGTTTGTA
6418  --+---------+---------+---------+---------+---------+-------  6477
      TGAAATAAGTTTAACCATAGCGGTTTTGGTTCTTCCTTGAGGGTAGGAGTTTCCAAACAT

      AGGAAGAATTCTCAGTCCAAAGCCTCAACAAGGTCAGGGTACAGAGTCTCCAAACCATTA
6478  --+---------+---------+---------+---------+---------+-------  6537
      TCCTTCTTAAGAGTCAGGTTTCGGAGTTGTTCCAGTCCCATGTCTCAGAGGTTTGGTAAT

      GCCAAAAGCTACAGGAGATCAATGAAGAATCTTCAATCAAAGTAAACTACTGTTCCAGCA
6538  --+---------+---------+---------+---------+---------+-------  6597
      CGGTTTTCGATGTCCTCTAGTTACTTCTTAGAAGTTAGTTTCATTTGATGACAAGGTCGT

      CATGCATCATGGTCAGTAAGTTTCAGAAAAAGACATCCACCGAAGACTTAAAGTTAGTGG
6598  --+---------+---------+---------+---------+---------+-------  6657
      GTACGTAGTACCAGTCATTCAAAGTCTTTTTCTGTAGGTGGCTTCTGAATTTCAATCACC

      GCATCTTTGAAAGTAATCTTGTCAACATCGAGCAGCTGGCTTGTGGGGACCAGACAAAAA
6658  --+---------+---------+---------+---------+---------+-------  6717
      CGTAGAAACTTTCATTAGAACAGTTGTAGCTCGTCGACCGAACACCCCTGGTCTGTTTTT

      AGGAATGGTGCAGAATTGTTAGGCGCACCTACCAAAAGCATCTTTGCCTTTATTGCAAAG
6718  --+---------+---------+---------+---------+---------+-------  6777
      TCCTTACCACGTCTTAACAATCCGCGTGGATGGTTTTCGTAGAAACGGAAATAACGTTTC

      ATAAAGCAGATTCCTCTAGTACAAGTGGGGAACAAAATAACGTGGAAAAGAGCTGTCCTG
6778  --+---------+---------+---------+---------+---------+-------  6837
      TATTTCGTCTAAGGAGATCATGTTCACCCCTTGTTTTATTGCACCTTTTCTCGACAGGAC

      ACAGCCCACTCACTAATGCGTATGACGAACGCAGTGACGACCACAAAAGAATTCCCTCTA
6838  --+---------+---------+---------+---------+---------+-------  6897
      TGTCGGGTGAGTGATTACGCATACTGCTTGCGTCACTGCTGGTGTTTTCTTAAGGGAGAT

                                                       SspI
                                                      ------
      TATAAGAAGGCATTCATTCCCATTTGAAGGATCATCAGATACTTAACCAATATTTCTC
6898  --+---------+---------+---------+---------+---------+----    6954
      ATATTCTTCCGTAAGTAAGGGTAAACTTCCTAGTAGTCTATGAATTGGTTATAAAGAG
```

Figure 1

PETUNIA HSP70-Fragment 1

5′-ACACAGAAAAATTTGCTACATTGTTTCACAAACTTCAAATATTATTCATTTATTT-3′ SEQ ID NO.1
3′-TGTGTCTTTTTAAACGATGTAACAAAGTGTTTGAAGTTTATAATAAGTAAATAAACAGTC-5′ SEQ ID NO.2

PETUNIA HSP70-Fragment 2

5′-GTCAGCTTTCAAACTCTTTGTTTCTTGTTTGTTGATTGAGAATAC-3′ SEQ ID NO.3
3′-GAAAGTTTGAGAAACAAAGAACAAACAACTAACTCTTATGGTAC-5′ SEQ ID NO.4

Figure 14

SOYBEAN HSP17.9

SEQ ID NO.5

5'-ACACAGAAACATTCGCAAAAACAAAATCCCAGTATCAAAATTCTTCTCTTTTTTTCATATTTCGCAAAGAC-3'

3'-TGTGTCTTTGTAAGCGTTTTTGTTTTAGGGTCATAGTTTTAAGAAGAGAAAAAAAGTATAAAGCGTTTCTGGTAC-5'

SEQ ID NO.6

Figure 15

MAIZE HSP70-FRAGMENT 1

5'-ACACTCTCTCGCCTGAGAAAAAAAATCCACGAACCAATTTCTCAGCAACCAGCAGCACG-3' SEQ ID NO.7

3'-TGTGAGAGAGCGGACTCTTTTTTTTAGGTGCTTGGTTAAAGAGTCGTTGGTCGTCGTGCTGGAC-5' SEQ ID NO.8

MAIZE HSP70-FRAGMENT 2

5'-ACCTGTGAGGGTTCGAAGGAAGTAGCAGTGTTTTTTGTTCCTAGAGGAAGAGC-3' SEQ ID NO.9

3'-ACTCCCAAGCTTCCTTCATCGTCACAAAAAACAAGGATCTCCTTCTCGGTAC-5' SEQ ID NO.10

Figure 16

SEQUENCE LISTING

```
(1) GENERAL INFORMATION:

   (iii) NUMBER OF SEQUENCES: 11


(2) INFORMATION FOR SEQ ID NO:1:

     (i) SEQUENCE CHARACTERISTICS:
          (A) LENGTH: 55 base pairs
          (B) TYPE: nucleic acid
          (C) STRANDEDNESS: double
          (D) TOPOLOGY: linear

    (ii) MOLECULE TYPE: DNA (genomic)

    (xi) SEQUENCE DESCRIPTION: SEQ ID NO:1:

ACACAGAAAA ATTTGCTACA TTGTTTCACA AACTTCAAAT ATTATTCATT TATTT          55


(2) INFORMATION FOR SEQ ID NO:2:

     (i) SEQUENCE CHARACTERISTICS:
          (A) LENGTH: 60 base pairs
          (B) TYPE: nucleic acid
          (C) STRANDEDNESS: double
          (D) TOPOLOGY: linear

    (ii) MOLECULE TYPE: DNA (genomic)

    (xi) SEQUENCE DESCRIPTION: SEQ ID NO:2:

CTGACAAATA AATGAATAAT ATTTGAAGTT TGTGAAACAA TGTAGCAAAT TTTTCTGTGT     60


(2) INFORMATION FOR SEQ ID NO:3:

     (i) SEQUENCE CHARACTERISTICS:
          (A) LENGTH: 45 base pairs
          (B) TYPE: nucleic acid
          (C) STRANDEDNESS: double
          (D) TOPOLOGY: linear

    (ii) MOLECULE TYPE: DNA (genomic)

    (xi) SEQUENCE DESCRIPTION: SEQ ID NO:3:

GTCAGCTTTC AAACTCTTTG TTTCTTGTTT GTTGATTGAG AATAC                     45


(2) INFORMATION FOR SEQ ID NO:4:

     (i) SEQUENCE CHARACTERISTICS:
          (A) LENGTH: 44 base pairs
          (B) TYPE: nucleic acid
          (C) STRANDEDNESS: double
          (D) TOPOLOGY: linear

    (ii) MOLECULE TYPE: DNA (genomic)

    (xi) SEQUENCE DESCRIPTION: SEQ ID NO:4:

CATGGTATTC TCAATCAACA AACAAGAAAC AAAGAGTTTG AAAG                      44


(2) INFORMATION FOR SEQ ID NO:5:

     (i) SEQUENCE CHARACTERISTICS:
          (A) LENGTH: 71 base pairs
          (B) TYPE: nucleic acid
          (C) STRANDEDNESS: double
          (D) TOPOLOGY: linear

    (ii) MOLECULE TYPE: DNA (genomic)
```

(xi) SEQUENCE DESCRIPTION: SEQ ID NO:5:

ACACAGAAAC ATTCGCAAAA ACAAAATCCC AGTATCAAAA TTCTTCTCTT TTTTTCATAT 60

TTCGCAAAGA C 71

(2) INFORMATION FOR SEQ ID NO:6:

(i) SEQUENCE CHARACTERISTICS:
(A) LENGTH: 75 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:6:

CATGGTCTTT GCGAAATATG AAAAAAAGAG AAGAATTTTG ATACTGGGAT TTTGTTTTTG 60

CGAATGTTTC TGTGT 75

(2) INFORMATION FOR SEQ ID NO:7:

(i) SEQUENCE CHARACTERISTICS:
(A) LENGTH: 59 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:7:

ACACTCTCTC GCCTGAGAAA AAAAATCCAC GAACCAATTT CTCAGCAACC AGCAGCACG 59

(2) INFORMATION FOR SEQ ID NO:8:

(i) SEQUENCE CHARACTERISTICS:
(A) LENGTH: 64 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:8:

CAGGTCGTGC TGCTGGTTGC TGAGAAATTG GTTCGTGGAT TTTTTTTCTC AGGCGAGAGA 60

GTGT 64

(2) INFORMATION FOR SEQ ID NO:9:

(i) SEQUENCE CHARACTERISTICS:
(A) LENGTH: 53 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:9:

ACCTGTGAGG GTTCGAAGGA AGTAGCAGTG TTTTTTGTTC CTAGAGGAAG AGC 53

(2) INFORMATION FOR SEQ ID NO:10:

(i) SEQUENCE CHARACTERISTICS:
(A) LENGTH: 52 base pairs
(B) TYPE: nucleic acid
(C) STRANDEDNESS: double
(D) TOPOLOGY: linear -continued

```
    (ii) MOLECULE TYPE: DNA (genomic)

        (xi) SEQUENCE DESCRIPTION: SEQ ID NO:10:

CATGGCTCTT CCTCTAGGAA CAAAAAACAC TGCTACTTCC TTCGAACCCT CA            52


(2) INFORMATION FOR SEQ ID NO:11:

     (i) SEQUENCE CHARACTERISTICS:
          (A) LENGTH: 597 base pairs
          (B) TYPE: nucleic acid
          (C) STRANDEDNESS: double
          (D) TOPOLOGY: linear

    (ii) MOLECULE TYPE: DNA (genomic)

        (xi) SEQUENCE DESCRIPTION: SEQ ID NO:11:

TCATCAAAAT ATTTAGCAGC ATTCCAGATT GGGTTCAATC AACAAGGTAC GAGCCATATC     60

ACTTTATTCA AATTGGTATC GCCAAAACCA AGAAGGAACT CCCATCCTCA AAGGTTTGTA    120

AGGAAGAATT CTCAGTCCAA AGCCTCAACA AGGTCAGGGT ACAGAGTCTC CAAACCATTA    180

GCCAAAAGCT ACAGGAGATC AATGAAGAAT CTTCAATCAA AGTAAACTAC TGTTCCAGCA    240

CATGCATCAT GGTCAGTAAG TTTCAGAAAA AGACATCCAC CGAAGACTTA AAGTTAGTGG    300

GCATCTTTGA AAGTAATCTT GTCAACATCG AGCAGCTGGC TTGTGGGGAC CAGACAAAAA    360

AGGAATGGTG CAGAATTGTT AGGCGCACCT ACCAAAAGCA TCTTTGCCTT TATTGCAAAG    420

ATAAAGCAGA TTCCTCTAGT ACAAGTGGGG AACAAAATAA CGTGGAAAAG AGCTGTCCTG    480

ACAGCCCACT CACTAATGCG TATGACGAAC GCAGTGACGA CCACAAAAGA ATTCCCTCTA    540

TATAAGAAGG CATTCATTCC CATTTGAAGG ATCATCAGAT ACTAACCAAT ATTTCTC       597
```

PROMOTER FOR TRANSGENIC PLANTS

This is a File Wrapper Continuation of application Ser. No. 08/366,240, filed Dec. 27, 1994 abandoned which is a continuation of application Ser. No. 08/172,334, filing date Dec. 22, 1993 now U.S. Pat. No. 5,378,619, which is a continuation-in-part of application Ser. No. 07/429,917, filed Oct. 31, 1989, now abandoned.

BACKGROUND OF THE INVENTION

This invention relates in general to plant genetic engineering. In particular, the present invention relates to a particular promoter from a figwort mosaic virus which is useful in the expression of genes in plants.

One of the primary goals of plant genetic engineering is to obtain plants having improved characteristics or traits. The type and number of these characteristics or traits are innumerable, but may include virus resistance, insect resistance, herbicide resistance, enhanced stability or improved nutritional value, to name a few. Recent advances in genetic engineering have enabled researchers in the field to incorporate heterologous genes into plant cells to obtain the desired qualities in the plant of choice. This permits advantageous genes from a source different than the transformed plant to be incorporated into the plant's genome. This new gene can then be expressed in the plant cell to exhibit the new trait or characteristic.

In order for the newly inserted gene to express the protein for which it codes in the plant cell, the proper regulatory signals must be present and in the proper location with respect to the gene. These regulatory signals include a promoter region, a 5' non-translated leader sequence and a 3' polyadenylation sequence. The promoter is a DNA sequence that directs the cellular machinery to produce RNA. The promoter region influences the rate at which the RNA product of the gene and resultant protein product of the gene is made. The 3'-polyadenylation signal is a non-translated region that functions in plant cells to cause the addition of polyadenylate nucleotides to the 3' end of the RNA to stabilize the RNA in the cytoplasm for subsequent translation of the RNA to produce protein.

It has previously been shown that certain promoters are able to direct RNA synthesis at a higher rate than others. These are called strong promoters. Certain promoters have also been shown to direct RNA production at higher levels only in particular types of cells and tissues. Those promoters that direct RNA production in many or all tissues of a plant are called constitutive promoters.

Previous work had shown that the 35S promoter from the cauliflower mosaic virus (CaMV35S) was the strongest constitutive promoter known in plants (Odell et al., 1985; Jensen et al., 1986; Jefferson et al., 1987; Kay et al., 1987; Sanders et al., 1987). This had been shown by demonstrating measurable levels of reporter gene proteins or mRNAs in extracts prepared from the leaves, stems, roots and flowers of transgenic plants. As a result, the CaMV35S promoter has been widely used by scientists in the field of plant genetic engineering.

Although the CaMV35S promoter appeared to be a strong, constitutive promoter in assays involving cell extracts, detailed histological analysis of a reporter gene product that is detectable at the cell and tissue level showed a rather high degree of variability of expression of this gene product. This histological analysis revealed an unknown and unexpected variability in the expression of a gene product driven by the CaMV35S promoter. This variable level and site of expression is believed to have two primary causes. The first is that variability is an intrinsic property of the CaMV35S promoter. The second is that the variability is caused by the position that the CaMV35S promoter driven DNA sequence is integrated into the genome of the transformed plant. When a gene is introduced into a plant cell, the new DNA becomes incorporated at random locations in the plant DNA. This variability in location or insert position leads to a variation in the level of promoter activity and protein production from individual transformants. As a result, a large number of individual transgenic plants must be assayed to find those that produce the highest levels of gene product in most or all of the tissues of the plants. Even the presumed strong, constitutive CaMV35S promoter is subject to the effect of insertion position variability and its use requires that a relatively large number of transformed plants be screened to find ones having appropriate levels of gene expression. Thus, it is clear that a need exists in plant genetic engineering for promoters that express high levels of chimeric gene product, but that is less subject to the wide variation in tissue level expression due to intrinsic properties of the promoter or caused by the effect of insertion position in transgenic plant DNA.

Other caulimoviruses, a group of double-stranded DNA viruses to which the cauliflower mosaic virus belongs, were considered as a potential source for such a promoter. Two caulimoviruses that are distantly related to CaMV have been previously described. The figwort mosaic virus (FMV) was described by Richins et al. (1987) and the carnation etched ring virus (CERV) was described by Hull et al. (1986). The DNA sequence and predicted gene organization of each of these two viruses were similar enough to the CaMV to permit Richins et al. to speculate as to the locations of the FMV and CERV homologues of the CaMV35S promoter. There was, however, little conservation of DNA sequences in these presumptive promoter regions and no confirming RNA transcript analysis had been carried out to provide a demonstration of the exact location of the promoter sequences, much less a showing that a promoter from FMV would provide an increased and more uniform level of expression of a chimeric gene in plants.

It is therefore a primary object of the present invention to provide a promoter for use in transgenic plants that exhibits an increased and more uniform level of expression of a gene product driven by the promoter than that exhibited by previously known plant promoters.

It is another object of the present invention to provide a promoter for use in transgenic plants that is less affected by insertion position effects than previously known and used plant promoters.

It is a further object of the present invention to provide a promoter for use in transgenic plants that exhibits a higher level of expression of a gene product driven by the promoter in many of the tissues and cells of the plant, particularly the floral buds, than that exhibited by previously known plant promoters.

It is yet another object of the present invention to provide such a promoter for the expression of a chimeric gene in plants that is obtained from the full-length transcript of the figwort mosaic virus.

Other and further objects of the invention will be made clear or become apparent from the following description.

BRIEF DESCRIPTION OF THE DRAWINGS

FIG. 1 shows the DNA sequence containing the full-length transcript promoter from the figwort mosaic virus including a 5' leader sequence and a small amount of 3' flanking DNA.

FIG. 14 illustrates the petunia HSP70 leader sequence (SEQ ID NO. 1, SEQ ID NO. 2, SEQ ID NO. 3, and SEQ ID NO. 4).

FIG. 15 illustrates the soybean HSP17.9 leader sequence (SEQ ID NO. 5 and SEQ ID NO. 6).

FIG. 16 illustrates the maize HSP70 leader sequence (SEQ ID NO. 7, SEQ ID NO. 8, SEQ ID NO. 9, and SEQ ID NO. 10).

SUMMARY OF THE INVENTION

Figure 2:
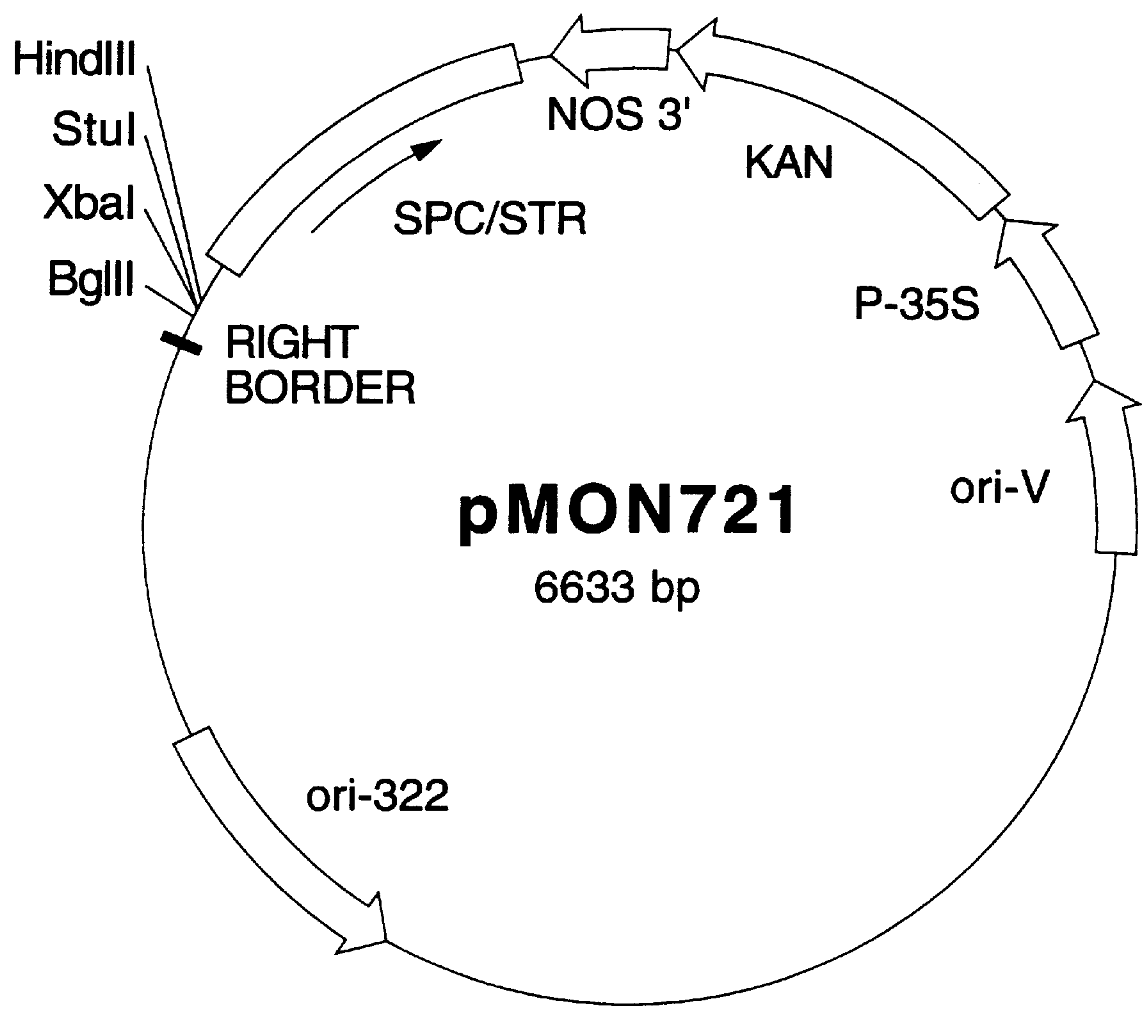
FIG. 2 shows a physical map of pMON721.

It has been discovered that the full-length transcript promoter from the figwort mosaic virus (FMV (SEQ ID NO. 11)) functions as a strong and uniform promoter for chimeric genes inserted into plant cells, particularly in the cells comprising the floral buds. The resulting transgenic plant expresses the protein encoded by the inserted gene at a higher and more uniform level throughout the tissues and cells of the transformed plant than the same gene driven by an enhanced CaMV35S promoter or by the CaMV35S promoter. The DNA sequence of the promoter is located between nucleotides 6368 and 6930 of the FMV (SEQ ID NO. 11) genome. A 5' non-translated leader sequence is preferably coupled with the promoter. The leader sequence can be from the FMV genome itself or can be from a source other than FMV. Preferred for the practice of the present invention are those 5' non-translated leader sequences selected from the group consisting of petunia HSP 70 (SEQ ID NO. 1, SEQ ID NO. 2, SEQ ID NO. 3, and SEQ ID NO. 4) (Winter et al. 1988); soybean HSP17.9 (SEQ ID NO. 5 and SEQ ID NO. 6) (Raschke et al. 1988); and the Maize HSP70 (SEQ ID NO. 7, SEQ ID NO. 8, SEQ ID NO. 9, and SEQ ID NO. 10) (Rochester et al. 1986). These synthetic oligonucleotides were designed as complimentary pairs which when annealed would generate a blunt 5' end, and would generate a 5' overhang at the 3' end which is compatible with and can be ligated to a DNA fragment restricted with Nco1. Each leader was also synthesized to contain the four nucleotides ACAC at the 5' end. These four nucleotides are the naturally occurring bases downstream of the start of CaMV transcription (Guilley et al. 1982) and were provided with each oligonucleotide to provide similar sequence context at the start of transcription for each leader construct. Similarly, a consensus sequence was used at the 3' end of the oligonucleotide to provide similar and near optimum sequence context at the start of translation (Kozak 1986).

Other aspects of the invention include use of the FMV promoter (SEQ ID NO. 11) in a method for transforming plant cells, a cassette vector including the FMV promoter, a chimeric gene including the FMV promoter sequence and transgenic plants, plant cells and seeds incorporating the FMV promoter in a chimeric gene.

DETAILED DESCRIPTION OF THE PREFERRED EMBODIMENT

The figwort mosaic virus (FMV) is a member of the caulimoviruses which are a group of double-stranded DNA viruses. Other members of this group include the cauliflower mosaic virus (CaMV) and the carnation etched ring virus (CERV). The CaMV and its promoter sequences are well-known in the literature (Gardner et al. 1981; Hohn et al. 1982; Guilley et al. 1982). The entire nucleotide sequence of the FMV DNA has been elucidated and reported by Richins et al. (1987). Richins et al. reported two intergenic regions in the FMV genome; a large intergenic region located between open reading frames (ORF) VI and VII and a small intergenic region located between ORFs V and VI. Richins et al. proposed that a promoter sequence analogous to the CaMV35S promoter, the major mRNA transcript promoter of the CaMV, was located in the large intergenic region of the FMV genome, but no confirming RNA transcript analysis had been carried out to provide a demonstration of the exact location of the transcriptional start and, consequently, the promoter sequence.

One aspect of the present invention includes isolation of the promoter for the full-length transcript from the figwort mosaic virus and the determination of the sequence of this promoter. The promoter preferably includes a 5' leader sequence that may be from the FMV promoter sequence itself or from a source heterologous with respect to the promoter.

The novel promoter of the instant invention was isolated from a small DNA fragment from a complete, full-length clone of FMV DNA. A plasmid, pFMVSc3, was obtained from Dr. R. J. Shepherd of the University of Kentucky. The nucleotide sequence of the FMV DNA and the organization of the FMV genome are given in Richins et al. (1987). This plasmid contains the complete DNA from FMV as adapted for growth on solanaceous hosts as described in Shepherd et al. (1987). As a result of the adaptation of the FMV DNA for growth on Solanaceous hosts, the FMV DNA is believed to have undergone a number of mutations at the nucleotide level. In the description and examples that follow FMV DNA from such an adapted strain is used. It is to be understood that the teachings and examples of this invention would also apply to a promoter region isolated from a "wild-type" or non-adapted FMV DNA with similar advantages and results. The original virus was isolated from *Scrophularia californica*. The FMV DNA was cloned into the unique SacI site of pUC13 (Vieira, J. and Messing, J., 1982) to obtain pFMVSc3. The nucleotide sequences shown in the drawing figures accompanying this disclosure that relate to FMV follow the numbering system used by Richins et al.

The FMV promoter sequence (SEQ ID NO. 11) was isolated by digesting pFMVSc3 with SspI which cleaves the FMV DNA at several sites including between nucleotides 6367 and 6368 and between nucleotides 6948 and 6949.

This releases a 581 base pair (bp) nucleotide fragment that contains a promoter sequence and 17 nucleotides of 5' non-translated leader sequence corresponding to the full-length transcript promoter of FMV (SEQ ID NO. 11). The nucleotide sequence of this fragment and a small amount of flanking DNA is shown in FIG. 1.

This fragment was purified using the NA-45 membrane method after electrophoretic separation on a 0.8% agarose gel and inserted into plasmid pMON721 that had been cleaved with StuI. A physical map of pMON721 is shown in FIG. 2.

Figure 3:
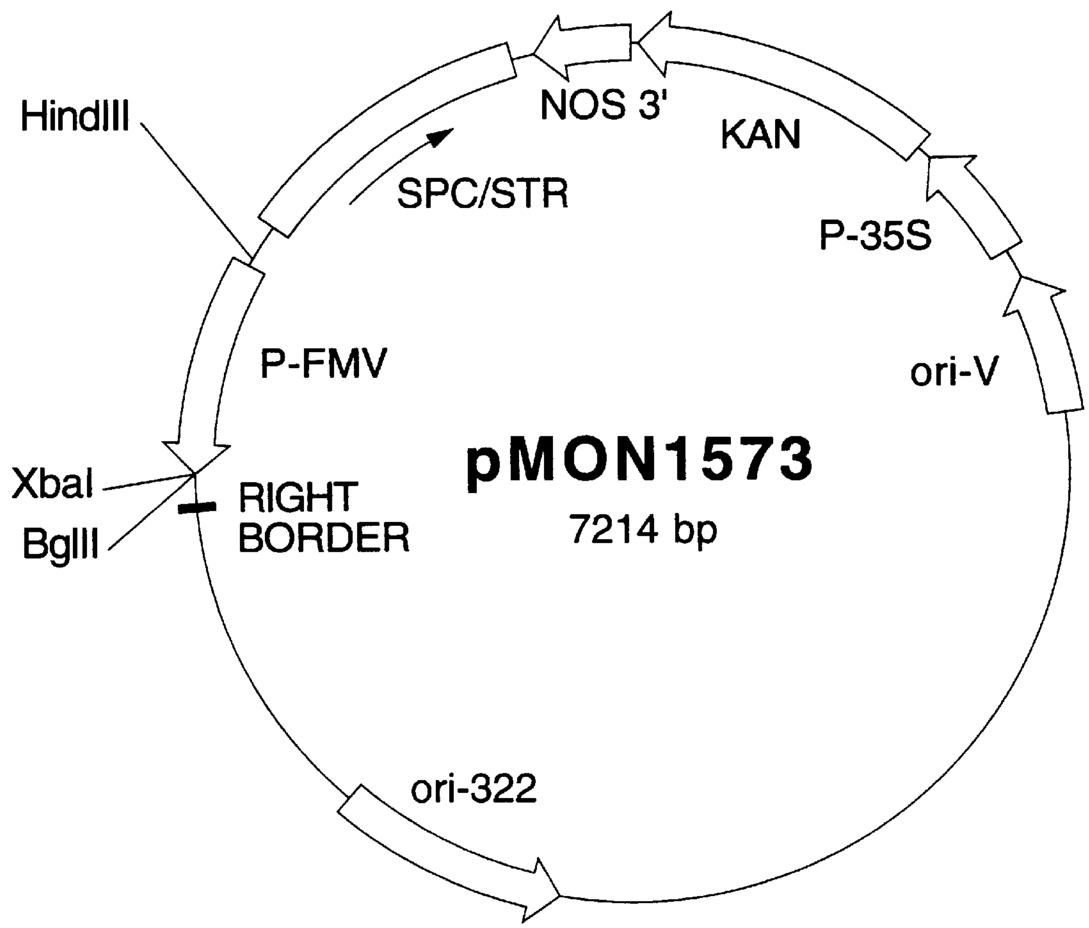
FIG. 3 shows a physical map of pMON1573.

As shown in FIG. 2, plasmid pMON721 contains a StuI site in a multilinker flanked by a HindIII site on one side and a BglII site on the other side. Once the SspI fragment was inserted into pMON721 at the StuI site, the resulting transformed pMON721 plasmids were screened for identification of transformants carrying the presumed FMV full-length RNA transcript promoter fragment oriented in the proper manner. A plasmid identified as pMON1573 was identified as containing the FMV promoter fragment (SEQ ID NO. 11) properly oriented so that the presumed 5' or upstream sequences of the promoter were adjacent to the HindIII site and the untranslated leader sequences terminated at the BglII site. FIG. 3 is a physical map of pMON1573.

Once a plasmid containing the FMV major RNA (full-length) transcript promoter sequence in the correct orientation was isolated, a cassette vector containing this promoter was prepared. A cassette vector is a cloning vector that typically includes all of the necessary elements needed for transformation of plants or plant cells. Typical plant cloning sectors comprise selectable and scoreable marker genes, T-DNA borders, cloning sites, appropriate bacterial genes to facilitate identification of transconjugates, broad host-range replication and mobilization functions and other elements as desired. A cassette vector containing the FMV major RNA transcript promoter of the present invention in a suitable plant transformation vector was prepared by starting with the pMON977 plasmid. A physical map of pMON977 is as illustrated in FIG. 4.

Figure 4:
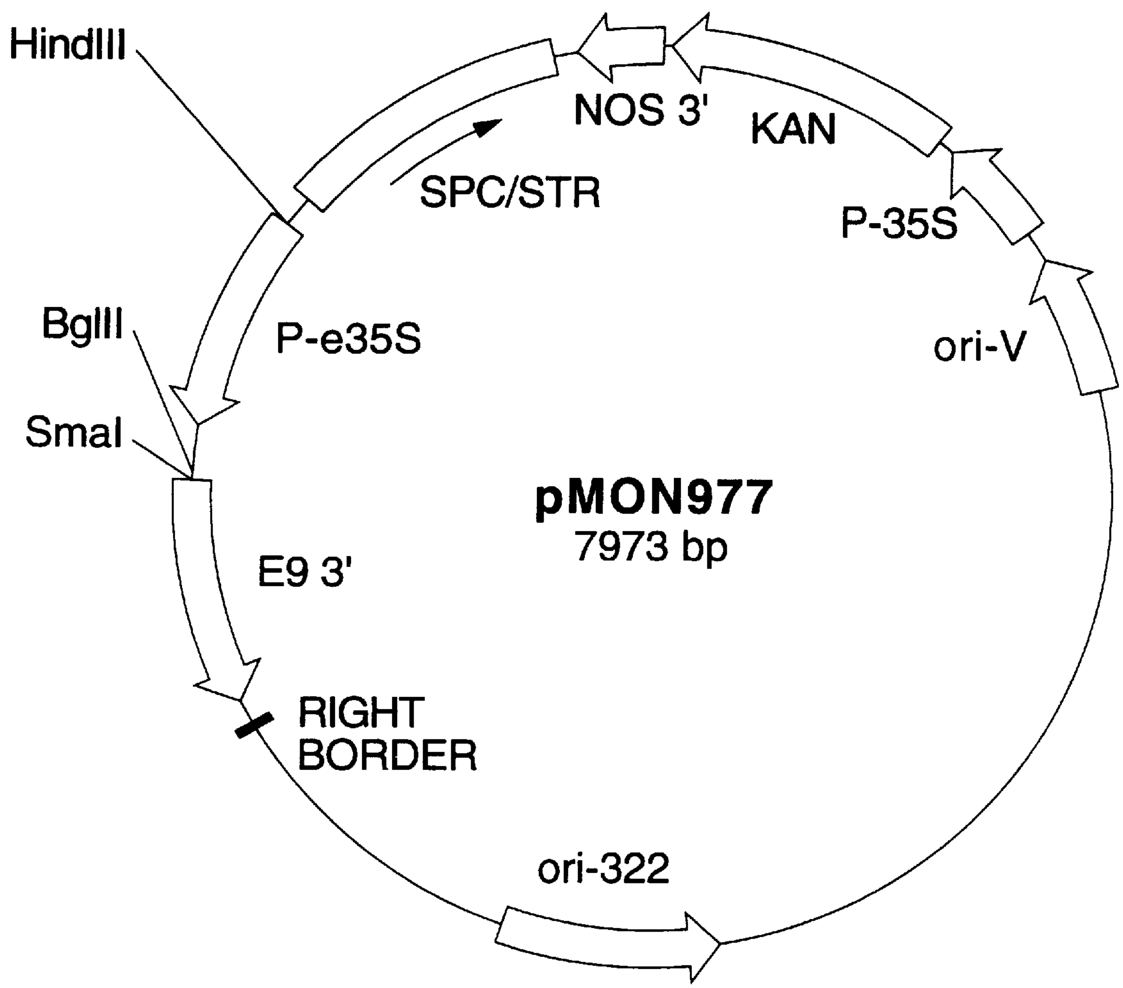
FIG. 4 shows a physical map of pMON977.
Figure 5:
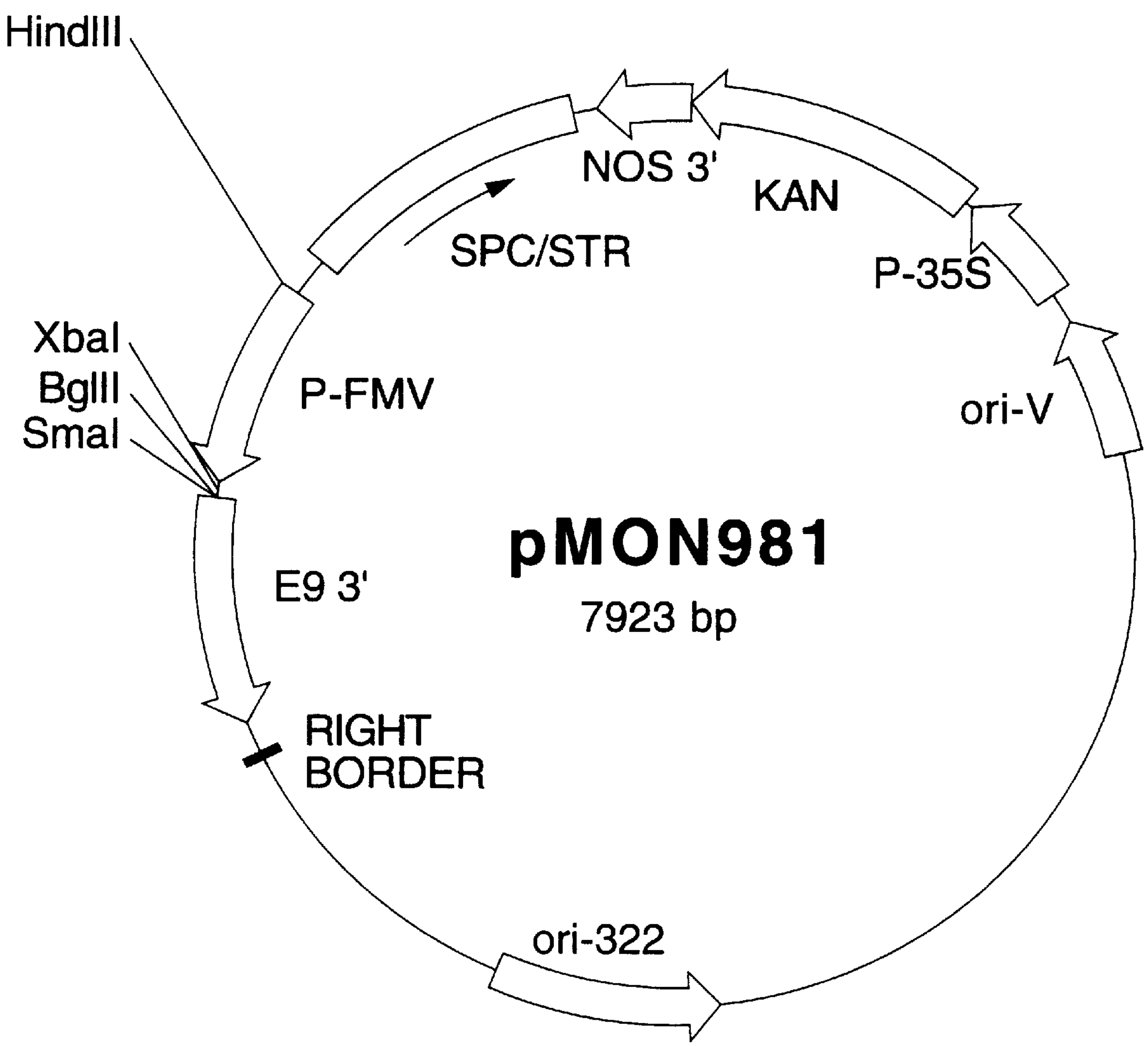
FIG. 5 shows a physical map of pMON981.

As shown in FIG. 4, pMON 977 has the following elements; a 0.93 kb fragment isolated from transposon Tn7 encoding a bacterial spectinomycin/streptomycin resistance gene (Spc/Str) that functions as a marker for selection of the plasmid in *E. coli* and Agrobacterium (Fling et al. 1985); a 1.61 kb segment of DNA encoding a chimeric kanamycin resistance gene (P-35S/Kan/NOS3') that permits selection of transformed plant cells (Beck et al. 1982); a 0.75 kb oriV DNA sequence containing the origin of replication from the Rk2 plasmid (Stalker et al. 1979); a 3.1 kb segment of pBR322 (ori-322) that provides the origin of replication for maintenance in *E. coli* and the bom site for the conjugational transformation to the Agrobacterium cells (Sutliffe 1979); a 0.36 kb segment from pTiT37 (the PvuI to BclI fragment) that carries the nopaline-type T-DNA right border (Fraley et al. 1985); and a 1.15 kb expression cassette consisting of the 0.66 kb enhanced 35S promoter P-e35S (Kay et al. 1987), several unique restriction sites and the 0.7 kb 3' non-translated region of the pea ribulose bisphosphate carboxylase small subunit E9 gene (E9 3') (Coruzzi et al., 1984 and Morelli et al., 1985). Plasmid pMON977 was cut with HindIII and BglII to remove the CaMV P-e35S enhanced 35S promoter. A 605 bp fragment containing the FMV full-length transcript promoter was excised from pMON1573 with HindIII and BglII and cloned into pMON977 to create pMON981. Plasmid pMON981 thus contains the FMV full-length transcript promoter and the E9-3' gene (FMV-E9 3') as an expression cassette. Also included in pMON981 between the FMV promoter and the E9-3' gene are restriction endonuclous sites for XbaI, BglII and SmaI. A physical map of pMON981 is shown in FIG. 5.

In order to determine that the isolated FMV sequence included the desired promoter region and to demonstrate the effectiveness and utility of the isolated FMV promoter, reporter genes were inserted into plant cassette vector pMON981. The reporter genes chosen were the *E. coli* β-glucuronidase (GUS) coding sequence and the Arabidopsis EPSP synthase gene containing a single glycine to alanine substitution which causes this enzyme to be tolerant of glyphosate herbicides.

Figure 6:
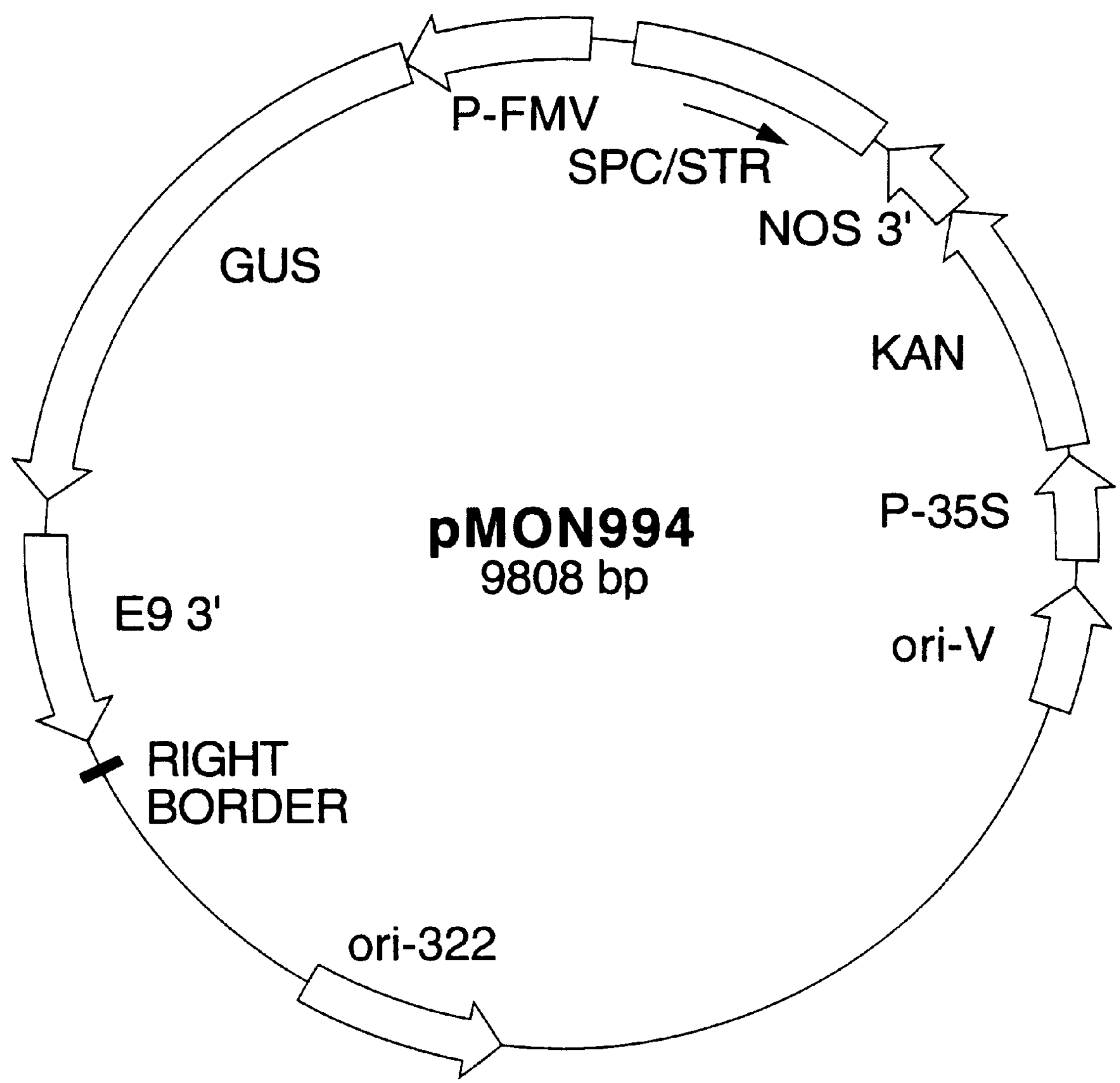
FIG. 6 shows a physical map of pMON994.
Figure 7:
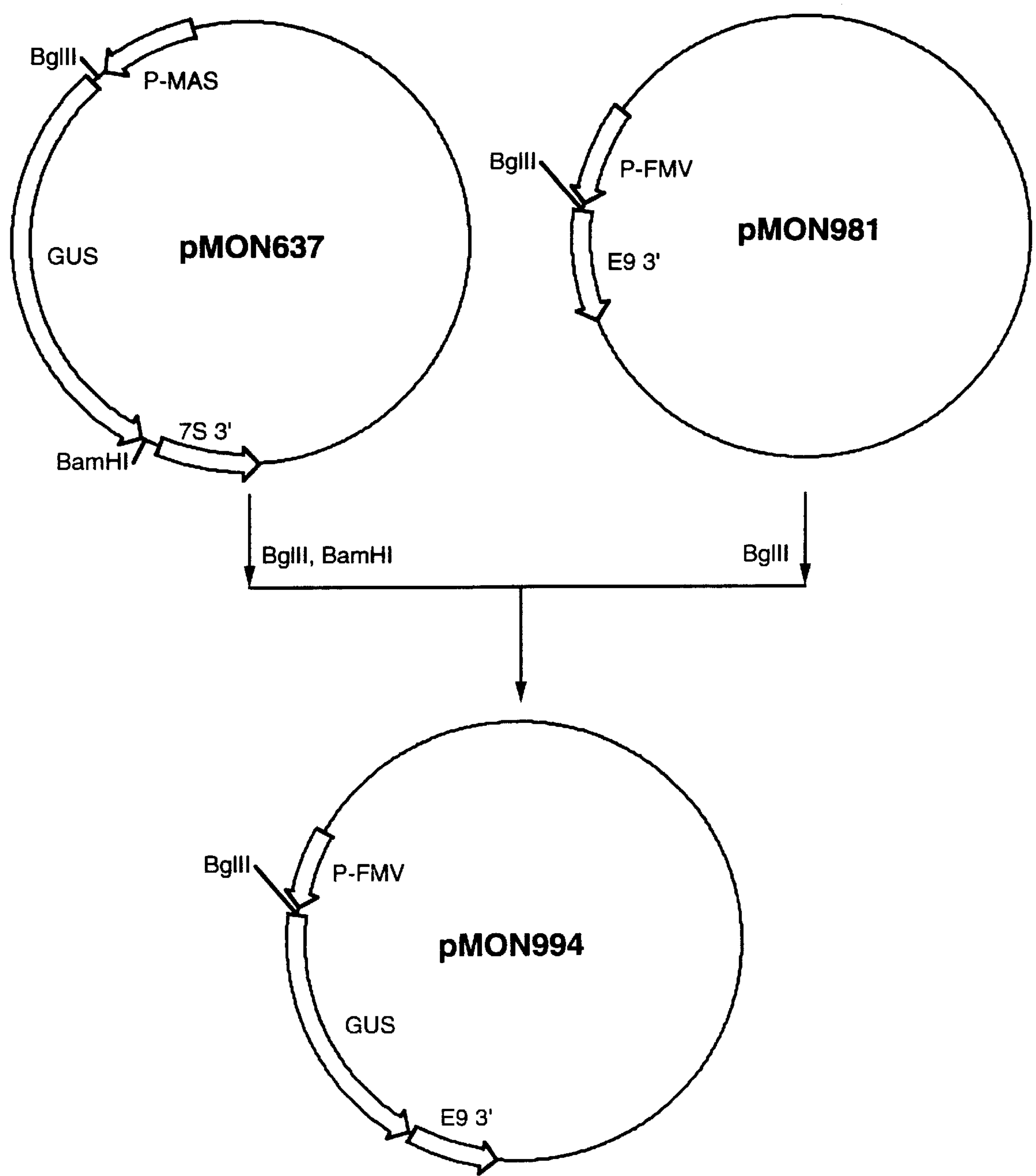
FIG. 7 shows the steps employed in the preparation of pMON994.

The *E. coli* β-glucuronidase coding sequence was inserted into the unique BglII site in the FMV-E9 3' cassette of plasmid pMON981. The GUS gene was excised from pMON637 on an 1885 bp BglII to BamHI fragment. The resulting plasmid was denoted pMON994 and contains the GUS gene under control of the FMV promoter. Plasmid pMON994 is shown in FIG. 6 and a flow chart illustrating the development of pMON994 is shown in FIG. 7.

EPSP synthase (5-enolpyruvyl-3-phosphoshikimate synthase; EC:25.1.19) is an enzyme involved in the shikimic acid pathway of plants. The shikimic acid pathway provides a precursor for the synthesis of aromatic amino acids essential to the plant. Specifically, EPSP synthase catalyzes the conversion of phosphoenol pyruvate and 3-phosphoshikimic acid to 5-enolpyruvyl-3-phosphoshikimic acid. A herbicide containing N-phosphonomethylglycine inhibits the EPSP synthase enzyme and thereby inhibits the shikimic acid pathway of the plant. The term "glyphosate" is usually used to refer to the N-phosphonomethylglycine herbicide in its acidic or anionic forms. Novel EPSP synthase enzymes have been discovered that exhibit an increased tolerance to glyphosate containing herbicides. In particular, an EPSP synthase enzyme having a single glycine to alanine substitution in the highly conserved region having the sequence: -L-G-N-A-G-T-A- located between positions 80 and 120 in the mature wild-type EPSP synthase amino acid sequence has been shown to exhibit an increased tolerance to glyphosate and is described in the commonly assigned patent entitled "Glyphosate-Tolerant 5-Enolpyruvyl-3-Phosphoshikimate Synthase" having U.S. Pat. No. 4,971,908, the teachings of which are hereby incorporated by reference hereto. Methods for transforming plants to exhibit glyphosate tolerance are discussed in the commonly assigned U.S. Pat. No. 4,940,835 entitled "Glyphosate-Resistant Plants," filed Jul. 7, 1986, the disclosure of which is specifically incorporated herein by reference. A glyphosate-tolerant EPSP synthase plant gene encodes a polypeptide which contains a chloroplast transit peptide (CTP) which enables the EPSP synthase polypeptide (or an active portion thereto) to be transported into a chloroplast inside the plant cell. The EPSP synthase gene is transcribed into mRNA in the nucleus and the mRNA is translated into a precursor polypeptide (CTP/mature EPSP synthase) in the cytoplasm. The precursor polypeptide is transported into the chloroplast.

Figure 8:
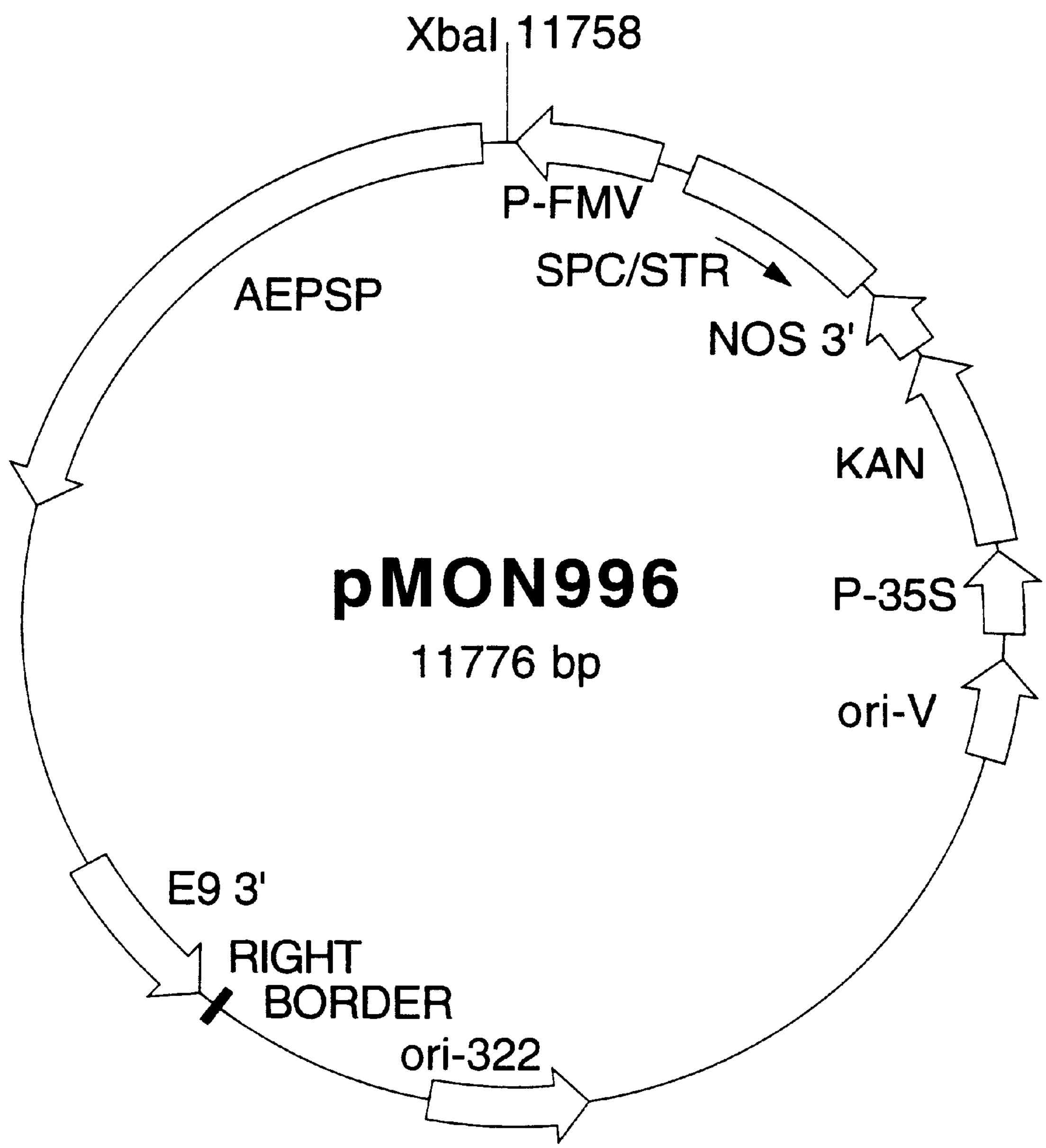
FIG. 8 shows a physical map of pMON996.
Figure 9:
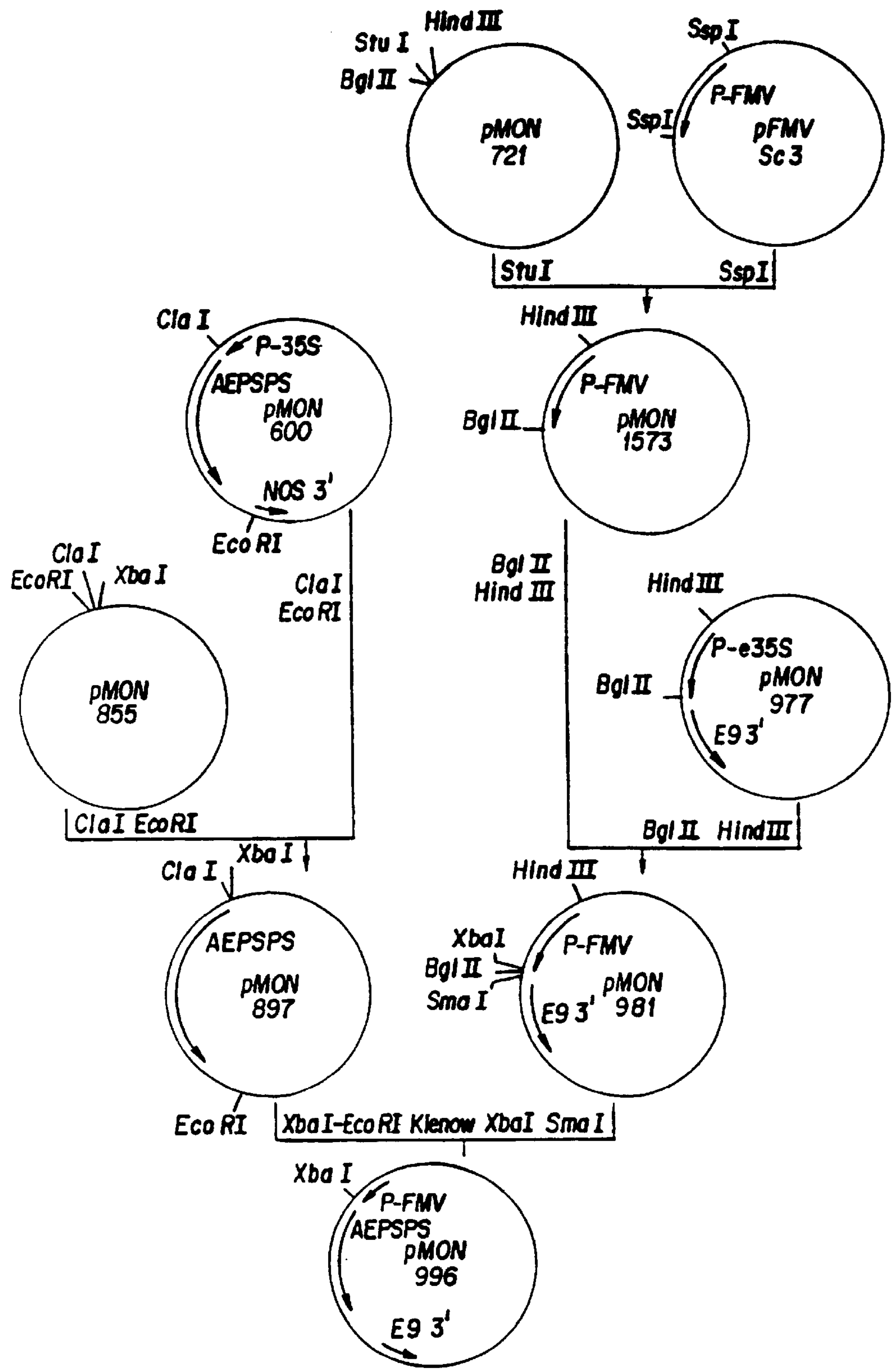
FIG. 9 shows the steps employed in the preparation of pMON996.

The EPSP synthase gene containing a single glycine to alanine mutation obtained from mutated *Arabidopsis thaliana* gene sequence was also inserted into the FMV-E9 3' cassette vector of plasmid pMON981. Plasmid pMON981 was cut with XbaI and SmaI. The Arabidopsis EPSP synthase gene is located on plasmid pMON897. Plasmid pMON897 is obtained by excising the Arabidopsis EPSP synthase gene (AEPSPS) in pMON600 by cutting with ClaI and EcoRI. This fragment is inserted into pMON855 which includes a multilinker containing sites for EcoRI, ClaI and XbaI. Plasmid pMON855 is cut with ClaI and EcoRI and the Arabidopsis EPSP synthase fragment isolated from pMON600 is inserted. The resulting plasmid is pMON897. Plasmid pMON897 was then cut with EcoRI and the ends were filled in using Klenow polymerase and then cut with XbaI and the Arabidopsis EPSP synthase gene was excised as a 3881 bp fragment. The Arabidopsis EPSP synthase gene was then cloned into pMON981 digested with XbaI and SmaI to create pMON996. A physical map of pMON996 is shown in FIG. 8 and a flow chart illustrating the development of pMON996 is shown in FIG. 9.

Once the FMV-E9 3' cassette vector containing the desired reporter gene is prepared, the vector can then be inserted into suitable Agrobacterium strains for Agrobacterium mediated transformation into plants or plant cells. The *Agrobacterium tumefaciens* strain to be used preferably contains a disarmed Ti plasmid. Two particularly useful strains are *Agrobacterium tumefaciens* strain A208 carrying the disarmed Ti plasmid pTiC58 derivative, pMP90RK (Koncz and Schell, 1986) and the ACO *Agrobacterium tumefaciens* strain carrying the disarmed pTiT37-CO nopaline type plasmid.

The *A. tumefaciens* strain 208 carrying the disarmed pMP90RK plasmid does not carry the T-DNA phytohormone genes and therefore cannot cause crown gall disease. When this strain is used for plant transformations, the vector plasmid is introduced into the Agrobacterium by the triparental conjugation system (Ditta et al. 1980) using the helper plasmid pRK2013. The vectors are transferred to plant cells by the vir functions encoded by the disarmed pMP90RK Ti plasmid. Analysis of transformants suggest that the vector is opened at the pTiT37 right border sequence and the entire vector sequence is inserted into the host plant chromosome. The pMP90RK Ti plasmid is probably not transferred to the plant cell but remains in the Agrobacterium.

Figure 10:
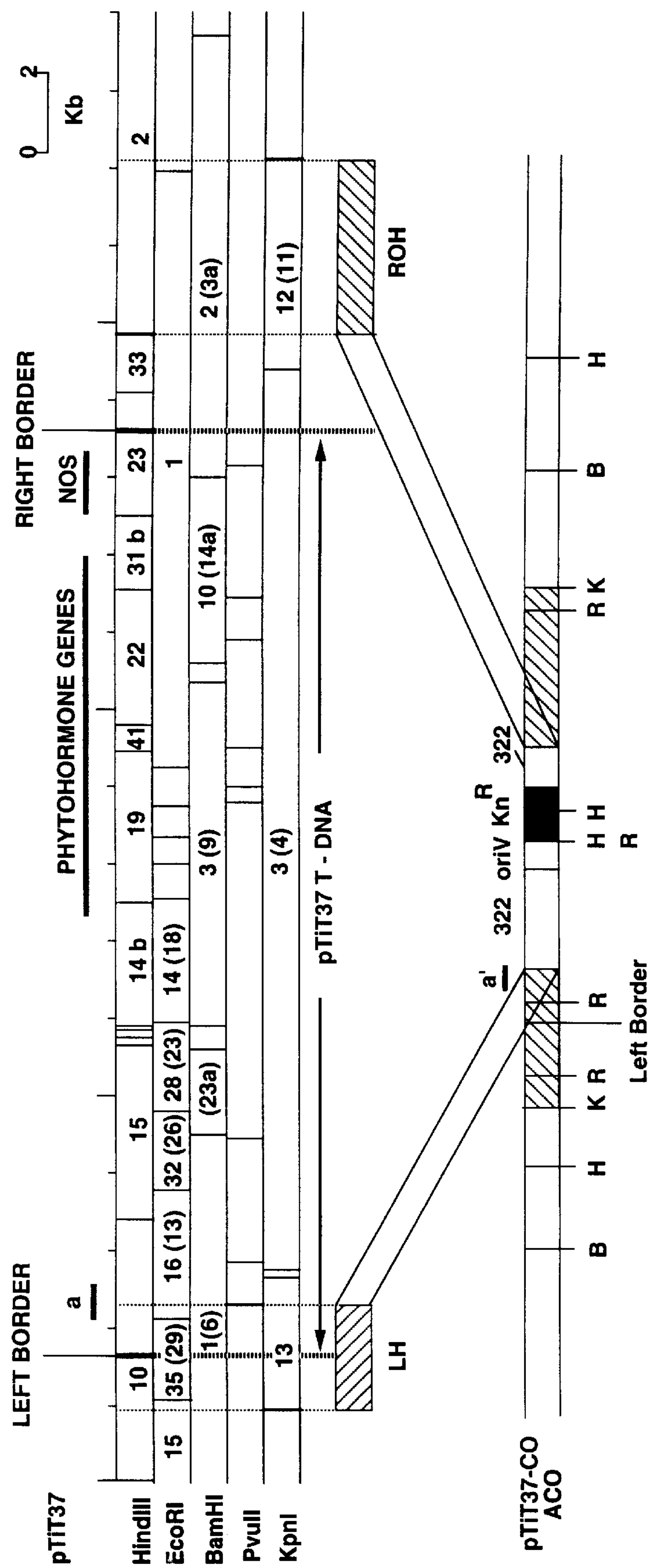
FIG. 10 shows a restriction map of the T-DNA regions of the *Agrobacterium tumefaciens* strain pTiT37 plasmid which was disarmed to create the ACO Agrobacterium strain.

FIG. 10 shows a restriction map of the T-DNA regions of the *Agrobacterium tumefaciens* strain pTiT37 plasmid which was disarmed to create the ACO Agrobacterium strain. This strain carries the disarmed pTiT37-CO nopaline type plasmid. The hatched boxes in FIG. 10 show the segments of the Ti plasmid DNA which were used to provide homology for recombination and replacement of the T-DNA. The T-DNA segment was replaced by the Tn601 bacteria kanamycin resistance gene ($Kan^R$) segment joined to the OriV and pBR322 segment homologous to the vectors described above. The recombination between the disarmed pTiT37-CO and plant cassette vector takes place through the pBR322 oriV area of homology resulting in the hybrid T-DNA which contains the entire DNA of the cassette vector plasmid. On cultivation of the Agrobacterium with plant cells, the hybrid T-DNA segment between the left and right borders is transferred to the cells and integrated into the genomic DNA.

Once the vector has been introduced into the disarmed Agrobacterium strain, the desired plant can then be transformed. Any known method of transformation that will work with the desired plant can be utilized. These methods include the leaf disc method of Horsch et al. (1984) and as adapted by Fry et al. (1986) for *Brassica napus*. Also conceived to be within the scope of the present invention is the use of DNA fragments or vectors including the FMV promoter sequences coupled with heterologous DNA sequences in the transformation of plants utilizing techniques such as electroporation or particle gun transformation.

Suitable plants for the practice of the present invention include, but are not limited to, soybean, cotton, alfalfa, oilseed rape, flax, tomato, sugar beet, sunflower, potato, tobacco, maize, wheat, rice and lettuce.

The effectiveness of the FMV promoter was determined by comparison studies with the enhanced CaMV35S promoter. In one study, pMON994 containing the FMV promoter including the 5' non-translated leader sequence from FMV fused to the β-glucuronidase reporter gene and the E9-3' non-translated polyadenylation region from pea was introduced into tobacco using the leaf disc method of Horsch et al. (1984) and transgenic plants obtained.

Tobacco (*Nicotiani tabacum* var. *samsun*) leaf disks with diameters of about 6 mm were taken from surface sterilized tobacco leaves. These were cultivated on MS104 agar medium for two days to promote partial cell wall formation at the wound surfaces. They were then submerged in a culture of *A. tumefaciens* cells containing both pMON994 and pMP90RK which had been grown overnight in Luria broth at 28° C., and shaken gently. The cells were removed from the bacterial suspension, blotted dry, and incubated upside down on filter paper placed over "nurse" cultures of tobacco cells as described by Horsch (1980). After two or three days, the disks were transferred to petri dishes containing MS media with 500 μg/ml carbenicillin with no nurse culture.

Control tissue was created using *A. tumefaciens* cells containing the helper plasmid pMP90RK and a different plant transformation vector, pMON505, which contained a T-DNA region with a NOS/NPTII/NOS kanamycin resistance gene and a NOS selectable marker gene identical to pMON994 , but without the FMV/β-glucuronidase gene.

Within ten days after transfer to the MS media, actively growing callus tissue appeared on the periphery of all disks on both the control and transformed plates.

Transformed tobacco plants were produced by regeneration from the above-described transformed leaf disks by the procedure described by Horsch, et al. (1985). The transformed plants obtained contained the pMON994 vector which contains the FMV promoter fused to the β-glucuronidase gene.

The same procedure as described above was utilized to obtain transformed tobacco plants containing the enhanced CaMV35S (CaMVe35S or P-e35S) promoter fused to the β-glucuronidase reporter gene and the E9-3' non-translated polyadenylation region from pea.

A second study involved obtaining transformed canola plants (*Brassica napus*) carrying the Arabidopsis EPSP synthase gene containing a single glycine to alanine substitution at amino acid 101 driven by either the FMV promoter or the CaMVe35S promoter. The pMON996 plasmid carrying the Arabidopsis EPSP synthase gene directed by the FMV promoter was introduced into canola by the method of Fry et al. (1986). Four terminal internodes from plants just prior to bolting or in the process of bolting, but before flowering were removed and surface sterilized in 70% v/v ethanol for one minute, 2% w/v sodium hypochlorite for twenty minutes, and rinsed three times in sterile distilled water. Stem segments were cut into 5 mm discs (Stringam 1977) and placed in a sterile 15×100 mm petri plate, noting the orientation of the basal end. The discs were inoculated for five minutes by pouring two to four milliliters of an overnight culture of the ACO *A. tumefaciens* strain containing pMON996 as previously described over the discs in the petri plate and then blotted dry by placing sterile filter paper in the petri plate and turning the plate over to absorb any excess bacteria. The stem discs were placed basal side down on feeder plates on medium containing 1/10× standard MS salts, B5 vitamins, 3% sucrose, 0.8% agar, pH 5.7, 1 mg/l BA and 1.4 ml TXD feeder cells (Horsch et al. 1985).

After a two to three day coculture period, stem discs were transferred, five to a deep dish petri plate (25×100 mm) containing the same medium with standard MS salts, 1 mg/l BA, 500 mg/l carbenicillin, 0.3 mm arginine, and 100 mg/l kanamycin for selection. At three weeks the stem explants were transferred to fresh plates containing the same medium. Culture of the explants was in a growth room under continuous cool white light at 26° C. Shoots that developed in the next one to three week period were excised from the stem explants, dipped in Rootone™ and placed in 2½ inch pots containing water saturated Metro Mix 350 in closed GAF containers for ten days in a chamber with a constant temperature of 21° C. and a 16 hour photoperiod. The shoots are assayed for the presence of kanamycin resistance immediately after being excised from the stem explant while still sterile.

This same procedure was used to obtain transformed canola plants containing the enhanced CaMVe35S promoter fused to the Arabidopsis EPSP synthase gene by inoculating the stem segment discs with ACO *Agrobacterium tunefaciens* strain containing pMON899.

EXAMPLE 1

Transformed plants containing the GUS gene driven by either the FMV full-length promoter or the enhanced CaMVe35S promoter were assayed using a histological staining procedure to determine GUS activity in the transformed cells. The results of these assays on plants transformed with pMON994 (FMV/GUS/E9) were compared to the results of the same assays performed on plants transformed with pMON977 (CaMVe35S/GUS/E9).

The histochemical assay of the tobacco plants containing the FMV/GUS/E9 and CaMVe35S/GUS/E9 constructs involved examination of young flower bud (10 mm) sections of the transformed plants to determine GUS activity. The flower bud section of the transformed plant was prepared by using a razor blade to free-hand section the plant tissue into sections less than 0.5 mm in thickness. The tissue was then placed in excess X-gluc solution so that the section was fully covered. Pulling a vacuum on the sections may aid in penetration of the X-gluc solution. A 50 ml X-gluc solution was prepared by combining 25 ml of 0.2M $Na_3PO_4$ buffer pH 7.0, 24.0 ml $dH_2O$, 0.25 ml 0.1M $K_3[Fe(CN)_6]$, 0.25 ml 0.1M $K_4[Fe(CN)_6]$ and 0.5 ml 1M EDTA, pH 7.0. To this solution, 50 mg of X-gluc (5-bromo-4-chloro-3-idolyl-β-glucuronide) obtained from Research Organics (Cleveland, Ohio) was added and stirred until dissolved. The solution was then preferably sterilized by filtration. The flower bud sections in the X-gluc solution were then placed at 37° C. for 2–4 hours. Care was taken to prevent evaporation of the solution. After the incubation period, the sections were rinsed with phosphate buffer, or distilled $H_2O$, and the sections were examined immediately with a dissecting scope or compound microscope. If there is interference from the pigments, the tissue can be fixed in FAA solution (85 ml 50% ethanol, 5 ml glacial acetic acid and 10 ml formalin) for 24 hours. Problems with phenolics can be mitigated by the addition of sodium metabisulfite to 20 mM to the staining solution just prior to staining. A positive test for the presence of GUS activity is shown by a blue coloration appearing in the tissue of the assayed plant section.

A histological staining assay was performed on a section of a tobacco flower bud transformed with the β-glucuronidase gene driven by either the enhanced CaMVe35S promoter or the full length FMV promoter of the present invention. A typical staining profile was observed for the CaMVe35S promoter driven GUS gene with staining in some tissues and no staining in other tissues within a single transgenic plant. The level of expression in those tissues expressing the GUS gene was considered fair. However, tissue from a plant transformed with the FMV promoter driven GUS gene showed that the transformed plant exhibited a much higher level of GUS expression and a more uniform pattern of expression throughout the tissue and cells. This was illustrated by the predominant blue coloration throughout the section.

The distribution of expression and the number of highly expressing transgenic plants obtained show that the FMV promoter is superior in tissue distribution and uniformity of expression when compared to the best enhanced CaMV promoter containing transformed plants. Greater than 90% of the FMV/GUS containing transformed plants showed very strong GUS expression and that the staining was uniform from plant to plant and tissue to tissue. This staining is consistently as good in the FMV containing plants as that in the best enhanced CaMV/GUS plants identified.

EXAMPLE 2

Transgenic plants containing the Arabidopsis EPSP synthase gene containing a single glycine to alanine mutation at nucleotide 101 driven by either the FMV promoter or the CaMVe35S promoter were obtained and analyzed for resistance to glyphosate. The transgenic plants containing the Arabidopsis EPSP synthase gene (as described) directed by the FMV promoter contained pMON996 while those plants containing the enhanced CaMVe35S promoter contained pMON899. These transgenic plants were planted and the seed from the $R_0$ plants harvested, threshed and dried before planting for a glyphosate spray test. The progeny were planted in 4-inch square pots of Metro 350 and three types of slow release fertilizers. A goal of twenty seedlings from each $R_0$ plant is desirable for testing. Germination frequency is usually high but overplanting ensures that twenty seedlings are present. The plants were thinned down by selecting the twenty most vigorous and erect seedlings seven to ten days after planting. A negative control (non-transformed, "Westar" variety) was planted at the same time to maintain quality and display the results. The plants were maintained and grown in a greenhouse environment. A sixteen-hour photoperiod and a temperature of 21° C. (day) and 15° C. (night) was maintained. Water soluble Peters Pete Lite® fertilizer with an analysis of 20-19-18 was applied once per week or as needed.

Two plants from each $R_0$ progeny were not sprayed and served as controls to compare and measure the glyphosate tolerance. When the remaining plants reached the six to eight leaf stage, usually 20 to 28 days after planting, glyphosate was applied at a rate equivalent to 0.28 Kg/ha. Low rate technology using low volumes has been adopted. A volume of ten imperial gallons for 0.28 Kg/ha of glyphosate is standard in field tests. A laboratory test sprayer had been calibrated to deliver a consistent rate equivalent to field conditions.

Figure 11:
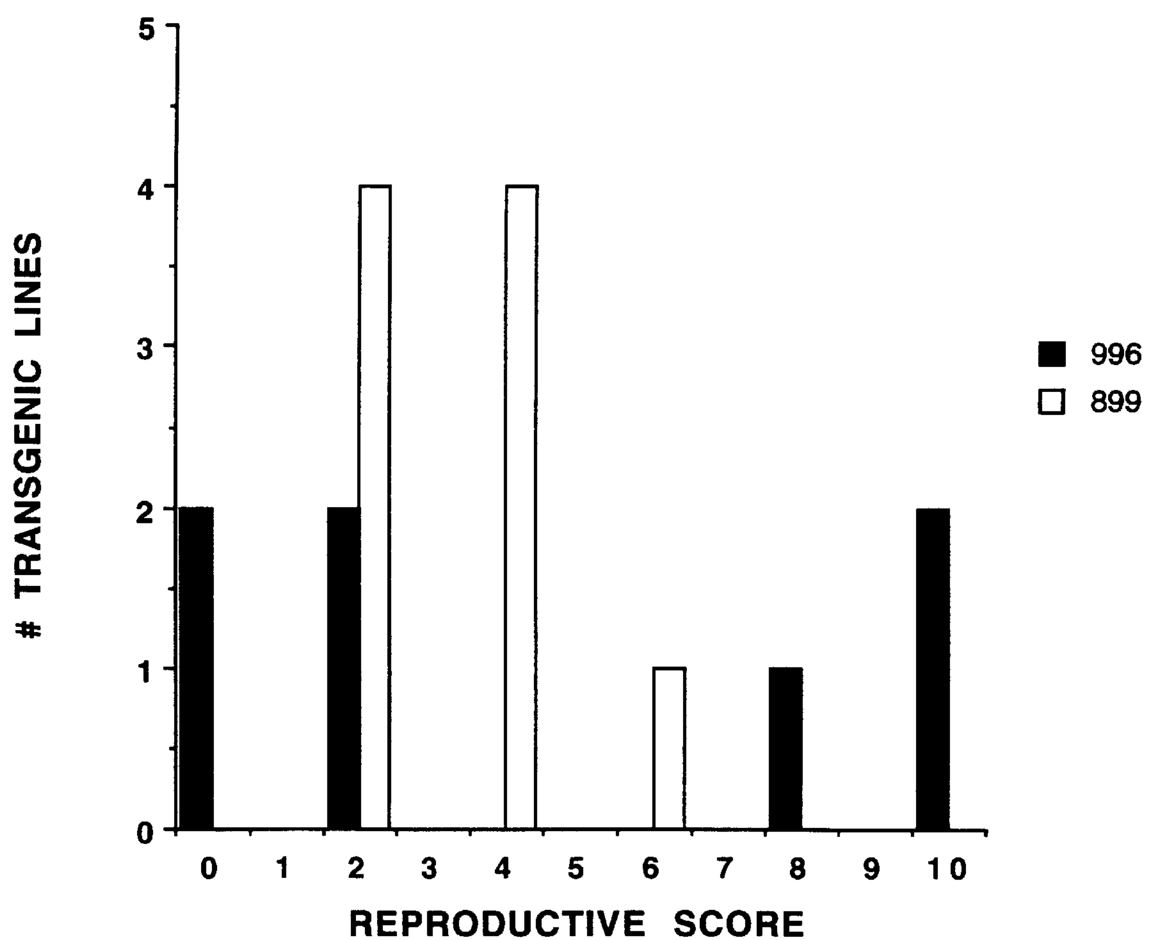
FIG. 11 shows the reproductive scores of transgenic plants containing mutant EPSPS under the control of the FMV (SEQ ID NO. 11) full-length transcript promoter (pMON996) or CaMVe35S promoter (pMON899) after glyphosate application.

Results of reproductive evaluations are shown in FIG. 11. These calculations are based upon a numerical scoring system relative to nonsprayed controls. Reproductive scores are examined at 28 days after spraying and are based upon six distinct conditions in which the main meristem or flowers reacted to the glyphosate. The scale used is:

0=no floral bud development

2=floral buds, but aborted prior to opening

4=flowers without antlers, antlers should protrude past petals

6=flowers with normal appearing antlers, but sterile

8=flowers with partially sterile antlers

10=fully fertile flowers

FIG. 11 compares the reproductive scores of the total number of transgenic canola lines containing the FMV promoter with transgenic lines containing the CaMVe35S promoter. As can be seen in FIG. 11, the reproductive scores of three of the seven transgenic lines containing the FMV promoter (pMON996) are better than any of the scores from lines containing the CaMVe35S promoter (pMON899). In fact, the transgenic lines containing pMON899 exhibit the highest levels of glyphosate tolerance among 150 lines previously tested. This demonstrates that the FMV promoter more uniformly expresses a gene product throughout the tissues and cells of the plant, and particularly in the floral buds. It is to be understood that an increased level of expression in the floral buds is important for maximal glyphosate resistance.

Comparison of Promoter Strength

In order to provide further evidence of the superior nature of the FMV35S promoter of the present invention, constructs were prepared which differed only in the promoter linked to the GUS gene. Those promoters were the full-length transcript promoters from CaMV and an isolate of FMV35S.

Figure 12:
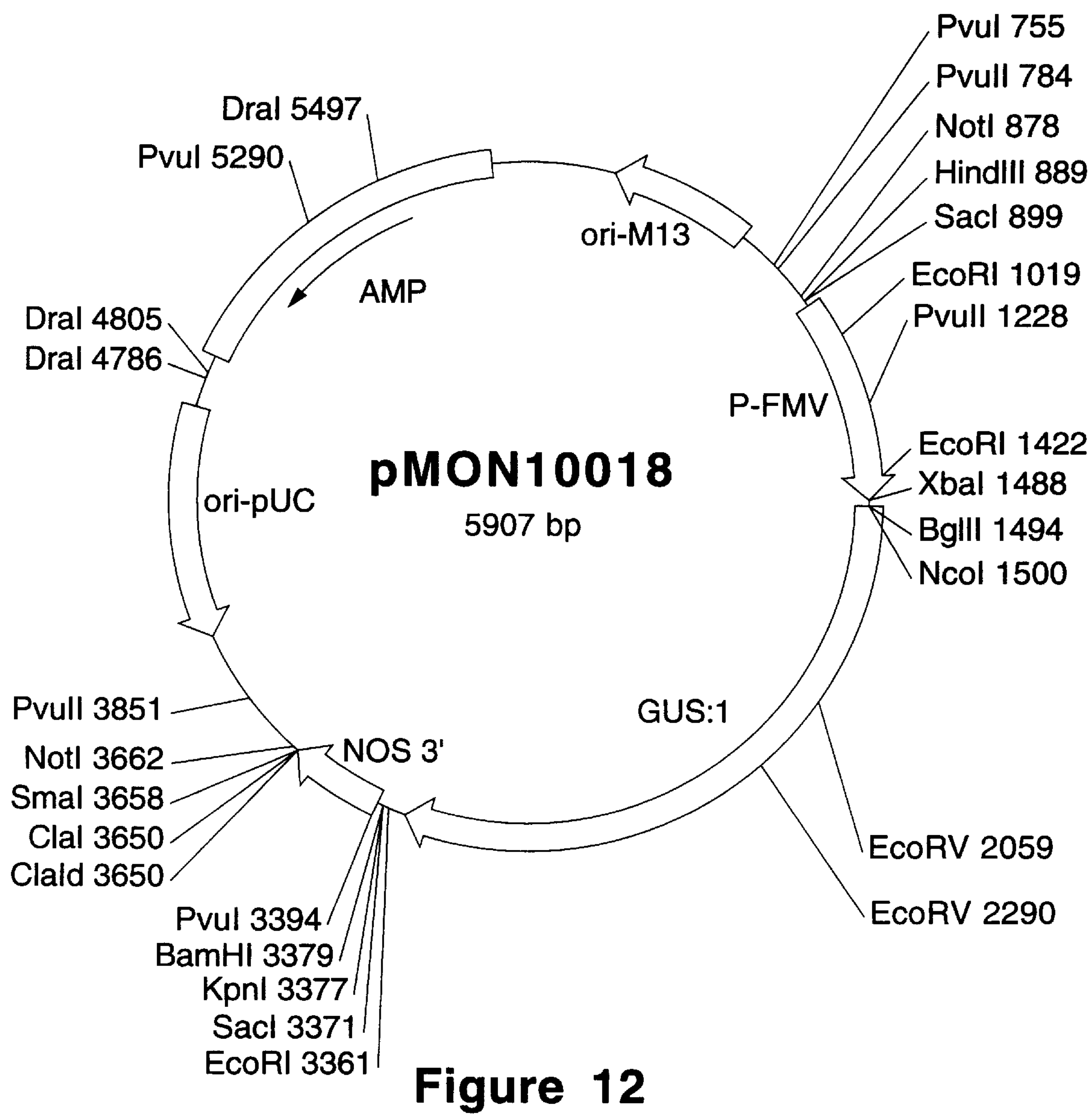
FIG. 12 illustrates pMON10018.
Figure 13:
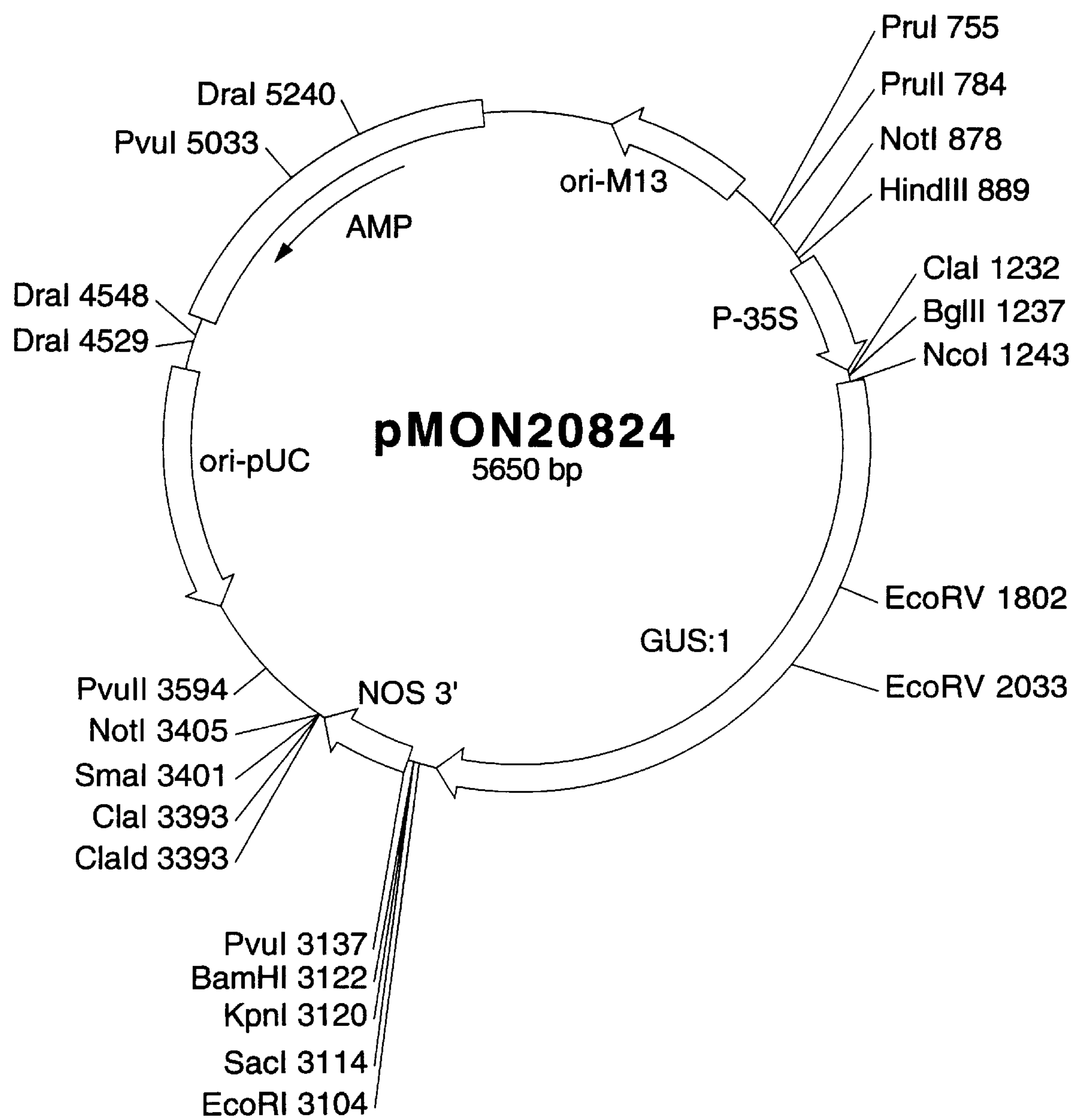
FIG. 13 illustrates pMON20824.

The 0.6 kb fragment of the 35S promoter from the FMV DxS strain (Richins et al.) was ligated to the 1.9 kb coding sequence for the β-glucuronidase (GUS) gene (Jefferson et al. 1987) and then ligated to the 0.3 kb 3' untranslated region of the nopaline synthase gene (NOS 3') (Fraley et al. 1983) in a derivative of pUC119 (Viera and Messing 1987). This resulted in pMON10018 (FIG. 12). The 350 bp CaMV35S promoter was cloned into pMON10018 replacing the FMV DxS promoter. This resulted in pMON20824 (FIG. 13).

Plant transformation vectors were prepared by digesting the plasmids pMON20824 and pMON10018 with Not I, recovering the fragment from each respective vector containing the promoter-GUS-NOS fragment, and religating the fragment into the Not I site of pMON17227. The plant transformation vectors were mobilized into *Agrobacterium tumifaciens* strain ABI using triparental conjugation as discussed above. *Nicotiana tabacum* plants were then transformed by the method of Horsch et al. (1985).

Transgenic *Nicotiana tabacum* plants (prepared as described above) containing the constructs were assayed for GUS activity using the fluorimetric assay of Jefferson et al. in extracted leaves, flowers, stems and roots. Incubations were performed at 37° C. for 15 minutes. A 1 g 4th internode leaf, a flower, a 4 cm long stem section, or roots were excised. Selected tissue was extracted by freezing in liquid nitrogen, grinding with a mortar and pestle, and resuspending in 1 ml 0.1M $K_3PO_4$, pH 7.8, 1 mM EDTA, 10 mM DTT, 0.8 mM PMSF, and 5% glycerol. The fluorogenic reaction was carried out in 2 mM 4-methyl umbelliferyl glucuronide. Fluorescence was measured using a Hoechst DNA fluorometer (Model TKO 100). Protein concentrations of plant extracts were determined by Bradford assay.

The CaMV35S promoter was set to 1 for each tissue analyzed and the relative expression levels of the FMV DxS promoter is provided in Table 1 below. The GUS expression obtained with the FMV35S promoter of the present invention is statistically superior to that obtained with the CaMV35S promoter, at the 95% confidence level, using a standard t-test of the means, in leaves, flowers, stems, and roots.

TABLE 1

| Tissue | Promoter | pMOL MU/ min/mg protein | Standard Error | Relative Expression | # lines |
|---|---|---|---|---|---|
| Leaves | CaMV 35S | 49602 | 9546 | 1 | 44 |
| | FMV 35S | 288794 | 46618 | 5.8 | 43 |
| Flowers | CaMV 35S | 200935 | 77806 | 1 | 40 |
| | FMV 35S | 3470289 | 1906995 | 17.3 | 30 |
| Stems | CaMV 35S | 35667 | 7815 | 1 | 42 |
| | FMV 35S | 76142 | 13854 | 2.1 | 42 |
| Roots | CaMV 35S | 225534 | 97729 | 1 | 39 |
| | FMV 35S | 569001 | 134337 | 2.5 | 30 |

The embodiments and examples described above are provided to better elucidate the practice of the present invention. It should be understood that these embodiments and examples are provided for illustrative purposes only, and are not intended to limit the scope of the invention.

References

Beck, E., Ludwig, G., Auerswald, E. A., Reiss, B., Shaller, H., *Gene,* 19:327 (1982)

Coruzzi, G., Broglie, R., Edwards, C., Chua, N. H., *EMBO J.,* 3:1671 (1984)

Fling, M. E., Kopf, J., Richards, C., *NAR,* 13:7095 (1985)

Fry, J., Barnason, A. and Horsch, R., *Plant Cell Reports,* 6:321–325 (1987)

Gardner, R. C. et al., *Nucleic Acids Research*, Vol.9, No. 12:287 (1981)

Guilley, H. et al., *Cell,* 30:763 (1982)

Hohn, T. et al., in Gene Cloning in Organisms Other than *E. coli*, p.193, Hofschneider and Goebel, eds. (Springer Verlag, N.Y., 1982)

Horsch R. and Jones G., *In Vitro,* 16:103–108 (1980)

Horsch R., Fry J., Hoffman, N., Wallworth, M., Eicholtz, D., Rogers, S., Fraley, R., *Science,* 227:1229–1231 (1985)

Hull, R., Sadler, J., Longstaff, M., *EMBO Journal*, Vol. 5, No. 12:3083–3090 (1986)

Jefferson, R. A., Kavanagh, T. A. and Bevan, M. W., *EMBO J.,* 6:3901–3907 (1987)

Jensen, J. S., Marcker, K. A., Otten, L. and Schell, J., *Nature,* 321:669–674 (1986)

Kay, R., Chan, A., Daly, M., McPherson, J., *Science,* 236:1299–1302 (1987)

Kozak, M. *Nature*, Vol. 315, pp. 200–204 (1986).

Odell, J. T., Nagy, F. and Chua, N. H., *Nature,* 313:810–812 (1985).

Raschke, E., Baumann, G., and Schöffl, F. (1988). Nucleotide sequence analysis of soybean small heat shock protein genes belonging to two different multigene families. *J. Mol. Biol.* 199, 549–557.

Richins, R., Scholthof, H., Shepherd, R., *Nucleic Acid Research,* 15, No. 20:8451–8466 (1987)

Rochester, D. E., Winter, J. A., and Shah. D. M. (1986). The structure and expression of maize genes encoding the major heat shock protein, hsp70. *EMBO* 5, 451–458.

Sanders, P. R., Winter, J. A., Barnason, A. R., Rogers, S. G. and Fraley, R. T., *Nucleic Acids Research,* 4:1543–1558 (1987)

Shepherd, R., Richins, R., Duffus, J., Hadley, M., *Phytopathology*, Vol. 77, No. 12:1668–1673 (1987)

Stalker, D. M., Kolter, R., Helinski, D., *Mol. Gen. Genet.,* 181:8 (1979)

Stringam, G. R., *Plant Science Letters,* 9:115–119 (1977)

Sutliffe, J., Cold Spring Harbor Symposium, 43:77 (1979)

Vieira, J. and Messing, J., *Gene,* 19:259 (1982); *Biochemicals for Molecular Biology*, p.126 (1989)

Winter, J., Wright, R., Duck, N., Gasser, C., Fraley, R., and Shah, D. (1988). The inhibition of petunia HSP70 messenger RNA processing during cadmium chloride stress. *Mol. Gen. Genet.* 211, 315–319.

I claim:

1. A full-length transcript promoter from figwort mosaic virus comprising nucleotides 11 through 573 of SEQ ID NO:11.

2. In a method for transforming a plant cell to express a chimeric gene, the improvement which comprises using a chimeric gene comprising operatively linked in sequence in the 5' to 3' direction:

a) a full-length transcript promoter from figwort mosaic virus that directs transcription of downstream DNA wherein said promoter comprises nucleotides 11 through 573 of SEQ ID NO:11;

b) a non-translated leader sequence;

c) a DNA sequence that is heterologous with respect to the promoter and causes the production of an RNA which hybridizes to the mRNA of a target gene; and d) a 3' non-translated DNA sequence which encodes a polyadenylation signal which functions in plant cells to cause the termination of transcription and the addition of polyadenylate nucleotides to the 3' end of the RNA.

3. A chimeric gene that functions in plant cells comprising operatively linked in sequence in the 5' to 3' direction:

a) a full-length transcript promoter from figwort mosaic virus that directs transcription of downstream DNA wherein said promoter comprises nucleotides 11 through 573 of SEQ ID NO:11;

b) a non-translated leader sequence;

c) a DNA sequence that is heterologous with respect to the promoter and causes the production of an RNA which hybridizes to the mRNA of a target gene; and d) a 3' non-translated DNA sequence which encodes a polyadenylation signal which functions in plant cells to cause the termination of transcription and the addition of polyadenylate nucleotides to the 3' end of the RNA.

4. A transformed plant cell that contains a chimeric gene that functions, in plant cells comprising operatively linked in sequence in the 5' to 3' direction:

a) a full-length transcript promoter from figwort mosaic virus that directs transcription of downstream DNA wherein said promoter comprises nucleotides 11 through 573 of SEQ ID NO:11;

b) a non-translated leader sequence;

c) a DNA sequence that is heterologous with respect to the promoter and causes the production of an RNA which hybridizes to the mRNA of a target gene, and d) a 3' non-translated DNA sequence which encodes a polyadenylation signal which functions in plant cells to cause the termination of transcription and the addition of polyadenylate nucleotides to the 3' end of the RNA.

5. A plant transformation vector which comprises a disarmed plant tumor inducing plasmid of Agrobacterium tumefaciens which is capable of inserting a chimeric gene into susceptible plant cells, wherein said chimeric gene comprises operatively linked in sequence in the 5' to 3' direction:

a) a full-length transcript promoter from figwort mosaic virus that directs transcription of downstream DNA wherein said promoter comprises nucleotides 11 through 573 of SEQ ID NO:11;

b) a non-translated leader sequence;

c) a DNA sequence that is heterologous with respect to the promoter and causes the production of an RNA which hybridizes to the mRNA of a target gene; and d) a 3' non-translated DNA sequence which encodes a polyadenylation signal which functions in plant cells to cause the termination of transcription and the addition of polyadenylate nucleotides to the 3' end of the RNA.

6. A transgenic plant which comprises plant cells of claim 4.

7. A seed from a plant of claim 6.

8. A seed of claim 7 in which said promoter comprises nucleotides 11 through 573 of SEQ ID NO:11.

9. A seed of claim 8 in which the chimeric gene expresses an RNA which hybridizes to the mRNA of a target gene.

* * * * *